United States Patent [19]
Schneider et al.

[11] Patent Number: 5,344,448
[45] Date of Patent: Sep. 6, 1994

[54] MULTI-FOCAL INTRA-OCULAR IMPLANT

[76] Inventors: Richard T. Schneider, 17 Alachua Highlands, Alachua, Fla. 32615; Richard H. Keates, 613 Nyes Pl., Laguna Beach, Calif. 92615

[21] Appl. No.: 28,630

[22] Filed: Mar. 9, 1993

Related U.S. Application Data

[63] Continuation of Ser. No. 833,775, Feb. 11, 1992, abandoned.

[51] Int. Cl.$^5$ ............................................. A61F 2/16
[52] U.S. Cl. ........................................ 623/6; 351/161
[58] Field of Search ..................... 623/6, 160 R, 161

[56] References Cited

U.S. PATENT DOCUMENTS

| | | |
|---|---|---|
| 3,034,403 | 5/1962 | Neefe . |
| 3,270,099 | 8/1966 | Camp . |
| 4,010,496 | 3/1977 | Neefe . |
| 4,402,579 | 9/1983 | Poler . |
| 4,435,856 | 3/1984 | L'Esperance . |
| 4,451,938 | 6/1984 | Kelman ................................. 623/6 |
| 4,512,040 | 4/1985 | McClure . |
| 4,525,043 | 6/1985 | Bronstein . |
| 4,619,657 | 10/1986 | Keates et al. . |
| 4,636,210 | 1/1987 | Hoffer ................................. 623/6 |
| 4,636,211 | 1/1987 | Nielsen et al. . |
| 5,026,396 | 6/1991 | Darin ................................. 623/6 |
| 5,089,024 | 2/1992 | Christie et al. . |

FOREIGN PATENT DOCUMENTS

| | | |
|---|---|---|
| 0140063A1 | 5/1985 | European Pat. Off. . |
| 3626869 | 2/1988 | Fed. Rep. of Germany .......... 623/6 |
| WO86/03961 | 7/1986 | PCT Int'l Appl. . |
| WO87/07496 | 12/1987 | PCT Int'l Appl. . |

OTHER PUBLICATIONS

Publication entitled "Ultrafocal® Bifocal Contact Lens", by Claud A. Kendall, pp. 31-35, dated Jan. 1976. Labelled Exhibit "A".

Primary Examiner—Randal L. Green
Assistant Examiner—Mary Beth Jones
Attorney, Agent, or Firm—Merchant, Gould, Smith, Edell, Welter & Schmidt

[57] ABSTRACT

A snap-together arrangement for a multi-focal lens is provided for use as an artificial lens implant in an eye from which the cataractous natural lens has been removed. The lens includes concentric lens portions secured together by an engagement arrangement to engage adjacent lens portions. Haptic members are provided to secure the lens in the eye.

11 Claims, 2 Drawing Sheets

MULTI-FOCAL INTRA-OCULAR IMPLANT

This application is a continuation application of Ser. No. 07/833,775, filed Feb. 11, 1992, now abandoned.

FIELD OF THE INVENTION

This invention relates generally to intra-ocular lenses. In particular, the invention concerns lenses useful as artificial lens implants in the eyes of patients from which natural lenses have been removed. More particularly, the invention concerns a snap-together arrangement usable to provide a multi-focal lens arrangement.

Background of the Invention

The implantation of an intra-ocular lens for restoring vision after cataract surgery is well known. Following extraction of a cataractous lens, an intra-ocular lens is normally implanted in either the anterior or the posterior chamber of the eye. For an anterior chamber implant, the lens is generally situated forward of, or mounted to, the iris. In the case of a posterior chamber implant, the lens is situated behind the iris and may be mounted within the cleft or fornix of the capsule, which remains in place after extra-capsular surgery.

For both anterior and posterior chamber implants, the artificial lens is usually centered and fixed in position by one or more supporting strands of haptic members. A typical haptic member is a flexible strand of non-biodegradable material which is fixed to the lens body, and exhibits specific spring-like memory qualities so that the haptic member can be readily compressed or offset from the normal rest position and which will thereafter readily return to the normal rest position.

Many intra-ocular implants generally include at least one lens surface curved to refract incoming light rays, thereby providing a desired power of correction. Generally, the degree of curvature of the lens surface, i.e., the radius of curvature or focal length of the lens surface helps define the power of the lens; the smaller the radius of curvature, the more incoming light rays are refracted and therefore the greater the corrective power of the lens.

The features that are possible in an intra-ocular lens are to a great extent dependent upon the method of manufacture used and/or the material from which the lens is made. A conventional method of making an intraocular lens is through a compression molding technique. For this technique, a mold is made by machining a cavity out of a piece of tool steel. The radius of curvature of the cavity is made equal to the radius of curvature of the convex side of the lens. The cavity is polished. Material for the lens, which typically has a consistency analogous to plexiglass, is generally manufactured in the form of rods preferably having an outside diameter equal to that of an intra-ocular lens to be produced in the mold. The material of the rod is cut into small disks which are heated and pressed in the polished mold. After cooling, the formed lens is released from the mold.

It is sometimes advantageous to include lens portions having different radii of curvature in a single lens so that in use the lens more adequately imitates the human lens. The human lens deforms to vary its focal length so that a person is able to focus on near objects and distant objects. This deformation process is called "accommodation". The process of accommodation is generally not available for intra-ocular lens implants. As a result, if the focal length of the lens is selected so that near objects will be properly focused, distant objects will not be properly focused. Similarly, if the focal length of the lens is selected so that far objects will be properly focused, near objects will not be properly focused.

Bifocal and multi-focal intraocular lens constructions have been described, for instance, in Applicants' application WO 87/07496, published Dec. 17, 1987 and in Nielson, et al., U.S. Pat. No. 4,636,211 both of which are incorporated herein by reference. For arrangements such as those described in these two references, a first lens portion has a focal length that is for viewing near objects and a second lens portion has a focal length that is for viewing distant objects, wherein when viewing an object each of the lens portions will produce an image. The clarity of each image will depend on the distance of the object, that is, one of the images will be relatively sharp and the other of the images will be relatively blurred. Under appropriate conditions, the images will be superimposed and the wearer's brain will evaluate and see the sharper, more intense, image. Preferably, the images from the lens portions are projected into the same plane. That is, the powers of the two lens portions should be selected so that the image from infinity projected through the second lens portion will be focused in the same plane as the image from a near object projected to the first lens portion. In a typical application, the power for the near vision portion should be selected for a "near" object spaced at a typical reading distance from the eye.

In some applications, different lens powers are accomplished through provision of a lens having portions of different radii of curvature. The lens may comprise a lens portion having a gradient, or continuously varying, radius of curvature. Alternatively, a single lens may include more than one discrete lens portion, with the lens portions having different indices of refraction. In some constructions both variations in radii of curvature and variation in indices of refraction may be used to define multi-focal arrangements.

The bi-focal or multi-focal lens arrangements described in WO 87/07496 are of generally two types. A first type is a target-like arrangement, including a central, generally circular curved lens portion, with at least one outer, annular, lens portion. The inner, circular lens portion has a lens surface having a first radius of curvature, and the other annular lens portion has a second lens surface having a second radius of curvature, different from the radius of curvature of the inner lens portion; that is, the inner portion is curved more severely than the outer portion. This difference in the radii of curvature causes the lens portions to have different corrective powers.

A second multi-focal lens arrangement is a chordal construction. In this arrangement, the lens includes semicircular lens portions of different corrective powers; that is, the generally circular lens is divided into two semicircular-shaped sections, each having a different radius of curvature, and therefore a different corrective power.

The procedures for producing a single lens are relatively complex, since known methods require machining and molding for each lens to the desired specifications. These specifications may vary greatly from user to user. Re-tooling for each prescription may be time consuming and therefore costly. It would be advantageous to standardize the production of multi-focal intraocular lenses while maintaining the flexibility to adapt each lens to the specification required by a particular user.

SUMMARY OF THE INVENTION

The present invention provides a readily assembled, snap-together multi-focal intra-ocular lens for implantation in an eye. Further, this invention provides a method of assembling a multi-focal lens including lens portions adapted for locking engagement.

A preferred multi-focal lens according to this invention includes a lens body having two or more lens portions or members arranged in a target-like arrangement. In a preferred embodiment, the first lens portion is generally circular and the second lens portion is generally annular, or ring-shaped, and defines a generally central circular aperture in which the first lens portion is positioned in use. In one preferred embodiment, when assembled the first and second lens portions are generally concentric. In some embodiments, a plurality of annular lens portions may be used, each fitting around another lens portion. In certain preferred embodiments, it may be preferred that each succeeding outer ring portion be slightly more flexible than its internal neighbor ring portion, to facilitate snapping the lens portions together, as will be described in great detail below.

The lens further includes engagement, interlocking, or fixing means, adapted for snap-fitting the first lens portion to the second lens portion (or fitting any two selected lens portions together). The preferred engagement means comprises first and second engagement members or pieces, each adapted to engage the other, as will be discussed further below. The first lens portion includes a first one of the engagement members and the second lens portion includes a second one of the engagement members. In a preferred embodiment, one engagement member is a lateral protrusion projecting from a circumferential surface of one lens portion; and the other engagement member is a receiving means adapted to receive the first engagement member such that the first lens portion is fixed to the second lens portion. In the preferred embodiment described in detail below, the first engagement member is a circumferential bead or lip member positioned on the circumference or periphery of the first lens portion; and, the second engagement member is an annular recess or groove on the second lens portion inner periphery, i.e. the periphery defining the central aperture. In an alternate embodiment of the lens, the engagement means first member is a resilient tang and the second member is an annular recess or channel.

In a typical application of the invention, the first lens portion includes a first (outer) lens surface curved generally continuously and having a first radius of curvature. The second lens portion includes a second (outer) lens surface curved generally continuously and having a second radius of curvature. In the preferred lens, the radii of curvature of the first and second (outer) lens portions are different. It is not required, however, that they be different. A variation in radius of curvature provides for different focal length. However, different indices of refraction for the material of the two lens portions may also be utilized to obtain different powers therein. In some situations, the desired optical power may require a different radius of curvature than is readily compatible with the neighboring ring. In such a situation, the lens designer may adjust the optical power not only with the radius of curvature, but also with the selection of a suitable "n" (refractive index). The term "outer" in this context is meant to refer to the lens surface oriented toward the object being viewed, in use. Another way to achieve the desired power is to provide a curved inner surface (i.e. the surface of the lens away from the object being viewed, in use). In the embodiments shown and described, the inner lens surface is planar, but it is contemplated that a convex or concave inner surfaces might also be used to achieve the desired optical power. In some applications both the inner and outer surfaces of the lens portions may be curved.

In one preferred embodiment, the inner lens portion has a focal length that is for viewing near objects and the outer lens portion has a focal length that is for viewing distant objects. If the relative powers are appropriately chosen, each of the lens portions will produce an image and the images will be superimposed, with one of the images relatively sharp and the other of the images will be relatively blurred, depending upon what is viewed. In some constructions, if appropriate powers are chosen, the blurred image will be less intense than the sharp image and the wearer's brain will evaluate and see the sharper image. Typically a difference in power between the lens portions of at least +3.0 diopters and preferably at least +3.5 diopters is needed, to achieve this effect.

Preferably, for best results in such constructions, the images from both lens portions should be projected into the same plane. That is, the powers of the two lens portions should be selected so that the image from infinity projected through the second lens portion will be focused in the same plane as the image from a close object being located at standard reading distance projected through the first lens portion.

A preferred method of manufacturing lenses according to this invention is by compression molding a disk with a spherical surface. The inner part of the disk may then be removed by a lathing process.

It is to be understood that more than two lens portions may be included in a multi-focal lens according to this invention. Further, while certain specific embodiments of the present invention are illustrated as described herein, the invention is not to be limited to the specific forms or arrangement of parts herein described and shown.

The drawings constitute a part of the specification and illustrate preferred embodiments of the invention. It will be understood that in some instances relative component sizes and material thicknesses may be shown exaggerated, to facilitate explanation.

BRIEF DESCRIPTION OF THE DRAWINGS

In the drawings, wherein like reference numerals indicate corresponding parts throughout the several views.

DETAILED DESCRIPTION OF THE INVENTION

Figure 1:
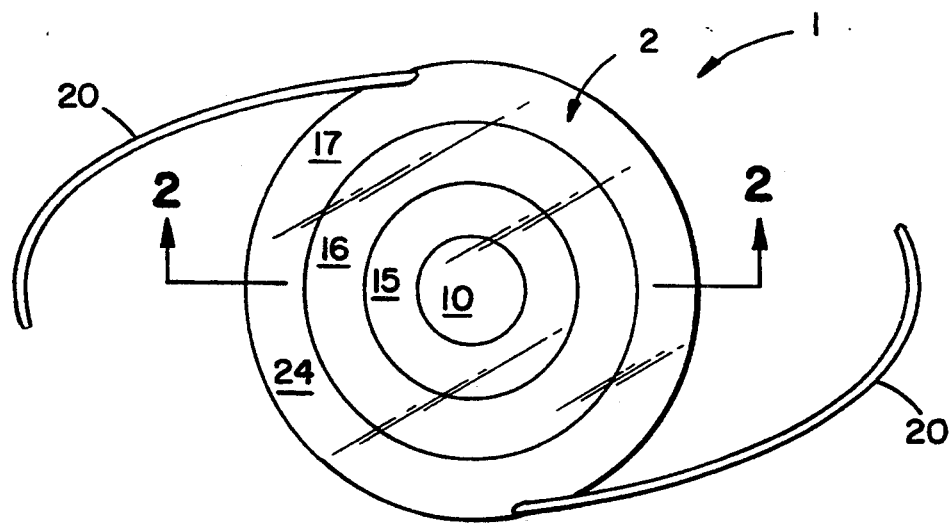
FIG. 1 is a top plan view of an intraocular lens construction according to the present invention, including concentric lens portion and haptic members.
Figure 2:
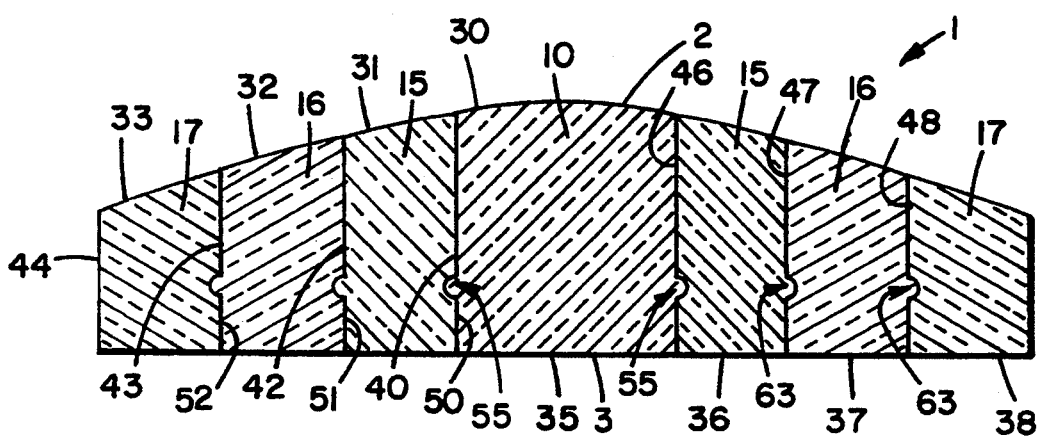
FIG. 2 is an enlarged fragmentary cross-sectional view taken generally along line 2—2, FIG. 1.
Figure 3:
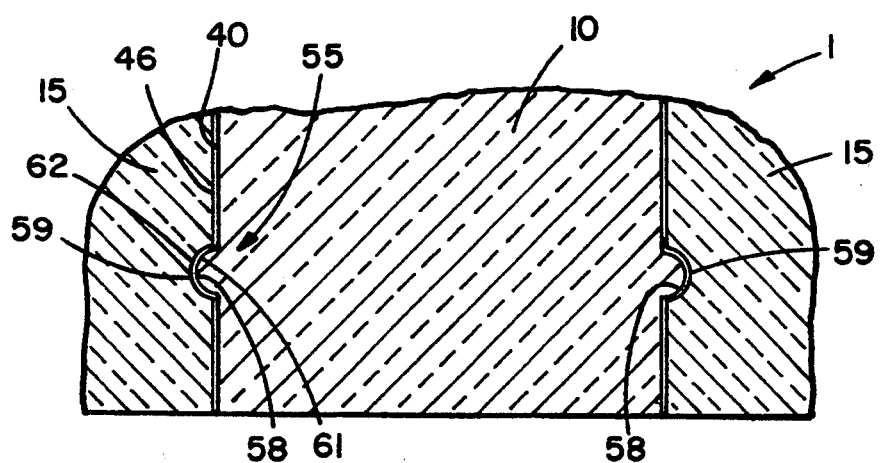
FIG. 3 is an enlarged fragmentary cross-sectional view of a portion of lens construction shown in FIG. 2, showing engagement means between adjacent lens portions.

FIGS. 1–3 show a preferred embodiment of a snap-together optically-offset intra-ocular lens construction 1, according to the present invention. As shown in FIG. 2, the preferred lens construction 1 has a first lens surface 2 and an opposite second surface 3. While surface 2 is shown convex, and surface 3 is flat, a variety of alternatives may be utilized in association with the present invention. More particularly, the arrangement of FIGS. 1–3 is plano/convex, but the principles on the invention may be utilized with alternative constructions.

Lens construction 1 includes an inner, generally central, circular lens portion 10 surrounded by a plurality of outer, annular, lens portions 15, 16, and 17, arranged in a target-like fashion. It is to be understood that an intra-ocular lens according to this invention may include a variety of numbers of annular lens portions. In some instances, only one annular lens portion will be preferred.

The preferred lens 1 further includes strand-like or haptic members 20, best shown in FIG. 1, which are used to position and fix the lens 1 to a portion of the eye, for instance, the iris. Generally, each haptic member 20 is a flexible strand of non-biodegradable material affixed to the lens construction 1. In the embodiment shown in FIGS. 1-3, the haptic members 20 are affixed directly to annular lens portion 17, which is the outermost lens portion. It is contemplated that a ring portion or member that is not a lens portion may circumscribe the outer-most lens portion. In such an arrangement, the haptic members might be secured to the non-lens ring portion. The preferred lens construction 1 shown includes two haptic members 20, however, alternate lens constructions may include more or fewer haptic members and still use the principles of the present invention.

Lens portions 10, 15, 16, and 17, have curved lens surfaces 30, 31, 32, and 33, respectively, as best shown in FIG. 2. Each lens surface 30, 31, 32, and 33 of the embodiment shown is defined by a different radius of curvature. In the construction 1 shown, lens surface 30 has a smaller radius of curvature than lens surface 31. Similarly, lens surface 31 has a smaller radius of curvature than lens surface 32, and lens surface 32 has a smaller radius of curvature than lens surface 33. Generally, the upper, refractive lens surface 2 is defined by and comprised of the lens surfaces 30-33. The lens portions 10, 15, 16, and 17 have bottom or lower surfaces 35, 36, 37, and 38, respectively, which generally comprise the lower surface of 3 of the lens 1.

Circular lens portion 10 has an outer peripheral surface 40, best shown in FIG. 2. Peripheral surface 40 is substantially circular. Annular lens portions 15, 16, and 17 similarly have outer peripheral surfaces 42, 43, and 44, respectively. Annular lens portions 15, 16, and 17 also have inner peripheral surfaces 46, 47, and 48, respectively, which are also substantially circular in the embodiments shown. Generally, the diameter of the outer peripheral surface of any given lens portion is substantially equal to, but slightly longer than, the diameter of the inner peripheral surface of the adjacent lens portion to provide for a snug, friction, nesting engagement as shown. Specifically, outer peripheral surface 40 has a diameter substantially equal to inner peripheral surface 46. Similarly, outer peripheral surface 42 has a diameter substantially equal to the diameter of inner peripheral surface 47; and, outer peripheral surface 43 has a diameter substantially equal to the diameter of inner peripheral surface 48. Diameter difference is exaggerated in FIG. 3 for illustration.

The annular lens portion inner peripheral surfaces 46, 47, 48 define generally central apertures 50, 51 and 52, respectively, illustrated in FIG. 2, which are generally circular. As shown in FIG. 2, lens portions 15, 16, and 17 include central apertures 50, 51, and 52, respectively.

Lens construction 1 includes engagement or fastening means (fastening arrangement) for securing adjacent lens portions. A preferred engagement means 55 is best illustrated in FIG. 3. The engagement means 55 includes a first lateral projecting portion or member 58 and a second projection-receiving portion or member 59. The preferred first member 58 includes a resilient bead or lip 61. The preferred second member 59 includes a recess or groove 62. Generally, in use, a resilient bead 61 of one lens portion (portion 10 in FIG. 3) is received in a recess 62 of an adjacent lens portion (portion 15 in FIG. 3). The preferred bead 61, FIG. 3, is substantially semi-circular in cross-section and extends from the outer peripheral surface of the associated lens portion. In the embodiment shown in FIG. 3, the bead 61 extends from outer peripheral surface 42 of circular lens portion 10 and is integral with the lens portion 10. Preferred recess 62 is generally semi-circular in cross-section and is sized to mate relatively tightly with bead 61. Recess 62 is defined in the inner peripheral surface of an annular lens portion. In the embodiment shown in FIG. 3, recess 62 is defined by inner peripheral surface 46 of annular lens portion 15.

It will be understood that a variety of engagement means may be utilized in association with the invention. For example, the bead or rib could alternatively be located on the "outer" of two engaging lens portions, with the groove or mating member on the associated "inner" lens portion.

The fastening means 55 described, and shown in FIG. 3, is the fastening means between lens portions 10 and 15 as indicated in FIG. 3. It is to be understood that fastening means 63, between other lens portions and shown in FIG. 2, are substantially similar to fastening means 55 and therefore are not further described. There is no requirement that all fastening means 63 of any given lens construction be the same, however it does provide convenience.

Figure 4:
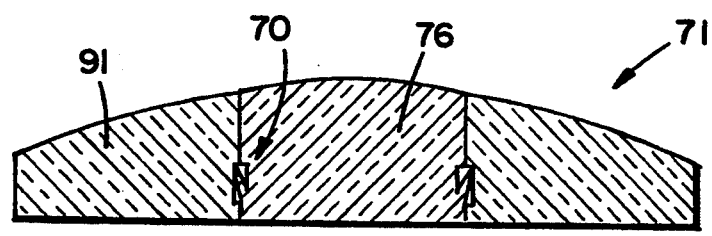
FIG. 4 is an enlarged fragmentary cross-sectional view of an alternate embodiment of an intraocular lens construction according to the invention taken generally in a manner analogous to FIG. 2.
Figure 5:
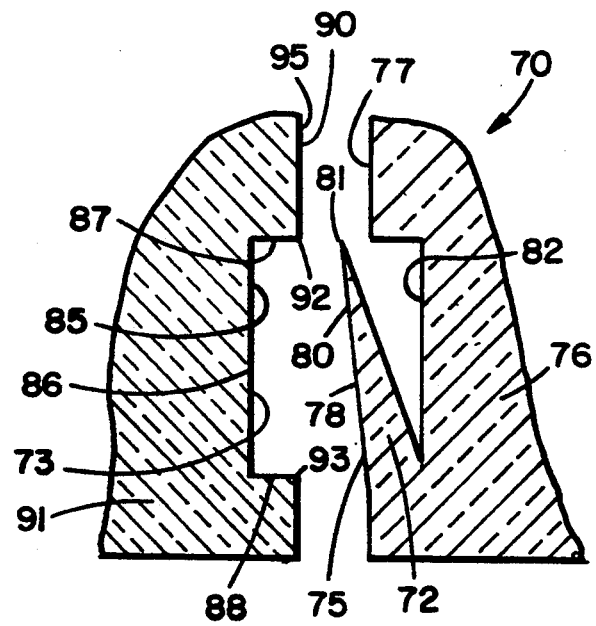
FIG. 5 is an enlarged fragmentary cross-sectional view of a portion of the lens construction shown in FIG. 4, showing alternate engagement means to the embodiment of FIG. 1.

An alternate engagement means 70 is shown in FIGS. 4 and 5, in association with a lens construction 71 such as that shown in FIG. 4. Alternate engagement means 70 includes a first engagement member 72 and a second engagement member 73. First engagement member 72 includes a resilient tang 75. Tang 75 is integral with, and extends from, central circular lens portion 76. The tang 75 protrudes beyond the outer peripheral surface 77 of lens portion 76. The tang 75 is generally triangular in cross-section, has an outer surface 78, and includes an end portion 80 having an apex 81. A cavity 82 is defined between tang 75 and outer peripheral surface 77.

The alternate engagement means second member 73 is a recess or channel 85. Recess 85 is defined by a back wall portion 86, an end wall portion 87, and an opposite-end wall portion 88. End wall portion 87 meets the inner peripheral surface 90 of the second lens portion 91 at corner 92. End wall portion 88 meets the lens portion inner peripheral surface 90 at corner 93.

In typical use, a lens construction such as lens construction 1 according to the present invention, is assembled by snapping selected lens portions (such as portions 10, 15, 16, and 17) together. A preferred method of producing such a lens is to choose a central lens portion 10 of the desired radius of curvature or power. An annular lens portion 15 is then chosen having the desired radius of curvature, and having an inner peripheral surface 46 diameter substantially equal to the diameter of the outer peripheral surface 40 of lens portion 10. Lens portion 10 is positioned with its bottom surface 35 generally near the lens surface 31 of lens portion 15, such that central lens portion 10 is aligned with central aperture 50. Lens portion 10 is then moved into position in aperture 50, by insertion therein. As lens portion 10 is inserted into central aperture 50, bead 61 slides along inner peripheral surface 46 of second annular lens portion 15. When lens portion 10 is fully inserted in second lens portion 15, bead 61 is aligned with recess 62 and securely mates therewith.

Similarly, lens portions 10 and 15, now joined, are inserted into the central aperture 51 of lens portion 16. Fastening means first member 58 of lens portion 16 engage fastening means second members 59 of lens portion 15, as described above. Similarly, lens portions 10, 15, and 16, now joined, are inserted into the central aperture 52 of lens portion 17. Fastening means first member 58 of lens portion 17 engage fastening means second member 59 of lens portion 16 in the manner described above. In this way, a lens having a central member and several annular members is formed simply by snapping adjacent lens portions in place.

For an alternate embodiment, shown in FIGS. 4 and 5, central lens portion 76 is inserted into the aperture 95 defined by annular lens portion 91, generally as described above with respect to the preferred embodiment. As lens portion 76 is inserted in aperture 95, resilient tang 75 is squeezed into cavity 82 by the inner peripheral surface 90 of the lens portion 91. When lens portion 76 has reached the proper place with respect to lens portion 91, tang apex 81 slides past corner 92 at the edge of recess 85. Resilient tang 75 springs outward from cavity 82, and the tang outer surface 78 contacts the back wall 86 of recess 85. Lens portion 76 is prohibited from linear displacement with respect to lens portion 91. Tang apex 81 abuts top wall 87 of recess 85, preventing upward movement of lens portion 76. Lens portion 76 is prevented from downward movement by contact between corner 93 and tang outer surface 78.

Thus far, embodiments of the invention have been described as comprising lens portions of different powers, wherein the different powers are provided by means of different radii of curvature on outer lens surfaces. In some applications, lens portions of different indices of refraction may be used to obtain different powers. In other applications, both index of refraction variations and curvature variations may be used to obtain different powers.

It will be understood that the present invention may be embodied in a variety of forms. The above descriptions, therefore, are not to be interpreted as limiting, but rather as a basis for the claims and as a basis for teaching persons skilled in the art the invention.

What is claimed is:

1. An intra-ocular lens adapted for use as an artificial lens implant, said intra-ocular lens comprising:

a) a lens body including a first inner lens portion having an outer periphery and a second outer lens portion having an inner periphery defining an aperture for receiving said first inner lens portion, said inner periphery of said second lens portion surrounding said outer periphery of said first lens portion:

i) said first lens portion having an outer lens surface and an inner lens surface, said outer periphery of said first lens being defined by a cylindrical surface, having a height positioned between said outer lens surface and said inner lens surface of said first lens ii) said second lens portion having an outer lens surface said inner periphery of and an inner lens surface, said second lens portion being defined by a cylindrical surface having a height positioned between said outer lens surface and said inner lens surface of said second lens portion;

b) engagement means including a lateral projection portion and a projection-receiving portion for releasably securing said first lens portion to said second lens portion, said lateral projection portion extending from one of said first lens portion or said second lens portion, said projection receiving portion defined by the other of said first lens portion or said second lens portion, wherein said outer lens surface of said first lens portion is adjacent to said outer lens surface of said second lens portion in non-overlapping relationship, wherein said inner lens surface of said first lens portion is adjacent to said inner lens surface of said second lens portion in non-overlapping relation, and wherein said cylindrical surface of said first lens portion is immediately adjacent to and facing said cylindrical surface of said second lens portion and wherein the heights of the two cylindrical surfaces are each substantially greater than a maximum dimension of the projection-receiving portion and of the lateral projection portion between the inner and outer lens surfaces of the first and second lens portions; said intraocular lens having first and second optical powers, said first optical power of said lens from said first lens portion and said second optical power of said lens from said second lens portion; and c) means for substantially non-movably retaining said lens implant within a chamber of a user's eye.

2. An intra-ocular lens according to claim 1 wherein said lateral projection portion is a resilient tang and said projecting-receiving portion is a recess for receiving said resilient tang, said tang defining a space between said tang and a remainder of said first lens portion or said second lens portion from which said tang extends.

3. An intra-ocular lens according to claim 1, wherein said lateral projection portion extends from said inner lens portion, and said outer lens portion defines said projection-receiving portion.

4. An intra-ocular lens according to claim 1, wherein said intra-ocular lens has first and second, opposite, lens surfaces, said first intraocular lens surface defined by said inner lens surfaces of said first and second lens portions and said second intraocular lens surface defined by said outer lens surfaces of said first and second lens portions; at least one of said first and second lens surfaces being convexly curved.

5. An intra-ocular lens according to claim 1, wherein said inner lens portion has a lower lens power than said outer lens portion.

6. An intra-ocular lens according to claim 1, wherein said retaining means includes at least one haptic member.

7. An intra-ocular lens according to claim 1, wherein said outer periphery of said first inner lens portion and said inner periphery of said second outer lens portion are circular.

8. An intra-ocular lens according to claim 1, wherein said first inner lens portion has a first optical power and said second outer lens portion has a second optical power, said first optical power being different from said second optical power.

9. A method of assembling a snap-together, multifocal intra-ocular lens, comprising the steps of:
   a) providing an annular lens portion having inner and outer lens surfaces and a cylindrical surface having a height positioned between said inner and outer lens surfaces of said annular lens portion; said annular lens portion having a first optical power; said annular lens portion further including a fastening means and a generally central aperture defined by said cylindrical surface;
   b) providing a circular lens portion having inner and outer lens surfaces and a cylindrical surface having a height positioned between said inner and outer lens surfaces of said circular lens portion, said circular lens portion having a second optical power different from said first power, and having a central focal axis co-linear with said aperture axis; said circular lens portion including fastening means constructed and arranged to engage said annular lens portion fastening means; and wherein the heights of the two cylindrical surfaces are each substantially greater than a maximum dimension of the fastening means between the inner and outer lens surfaces of the annular lens and circular lens portions; and
   c) inserting said circular lens portion into said annular lens portion aperture until said annular lens portion fastening means engages said circular lens portion fastening means, thereby securing said circular lens portion with said annular lens portion, wherein said inner lens surfaces are adjacent to one another in non-overlapping relation, wherein said outer lens surfaces are adjacent to one another in non-overlapping relation, and wherein said cylindrical surface of said first lens portion is immediately adjacent to and facing said cylindrical surface of said second lens portion, said first optical power of said lens from said first lens portion and said second optical power of said lens from said second lens portion.

10. A method of assembling a snap-together intra-ocular lens, comprising the steps of:
   a) providing a first lens portion having inner and outer lens surfaces having a height and a cylindrical surface positioned between said inner and outer lens surfaces of said first lens portion; said first lens portion having a first optical power; said first lens portion including a region having a circumferential inner periphery defined by said cylindrical surface and defining an aperture; said inner periphery including first lens portion fastening means for fastening said first lens portion to another lens portion;
   b) providing a second lens portion having inner and outer lens surfaces and a cylindrical surface having a height positioned between said inner and outer lens surfaces of said second lens portion; said second lens portion having a second optical power; said second lens portion including an outer periphery defined by said cylindrical surface of said second lens portion; said outer periphery including second lens portion fastening means constructed and arranged to engage said first lens portion fastening means; and wherein the heights of the two cylindrical surfaces are each substantially greater than a maximum dimension of the fastening means between the inner and outer lens surfaces of the first and second lens portions; and
   c) inserting said outer periphery of said second lens portion into said aperture defined by said inner periphery of said first lens portion until said first lens portion fastening means engages said second lens portion fastening means, thereby securing said outer periphery of said second lens portion within said inner periphery of said first lens portion, wherein said inner lens surfaces are adjacent to one another in nonoverlapping relation, wherein said outer lens surfaces are adjacent to one another in non-overlapping relation and wherein said cylindrical surface of said first lens portion is immediately adjacent to and facing said cylindrical surface of said second lens portion.

11. A method according to claim 10, wherein the optical power of the first lens portion is different from the optical power of the second lens portion.

* * * * *

UNITED STATES PATENT AND TRADEMARK OFFICE
CERTIFICATE OF CORRECTION

Page 1 of 2

PATENT NO. : 5,344,448
DATED : September 6, 1994
INVENTOR(S) : Richard T. Schneider et al.

It is certified that error appears in the above-indentified patent and that said Letters Patent is hereby corrected as shown below:

Column 1, line 48, delete "intraocular", insert "intra-ocular".

Column 2, line 6, delete "intraocular", insert "intra-ocular".

Column 4, line 56, delete "intraocular", insert "intra-ocular".

Column 4, line 66, delete "intraocular", insert "intra-ocular".

Column 5, line 16, delete "on", insert "of".

Claim 1, Column 8, line 10, add "portion" after "lens".

Claim 1, Column 8, line 12, add "portion" after "said first lens".

Claim 1, Column 8, line 14, delete "said inner periphery of".

Claim 1, Column 8, line 15, add "said inner periphery of" after "surface,".

Claim 1, Column 8, line 41, delete "intraocular", insert "intra-ocular".

Claim 1, Column 8, line 60, delete "intraocular", insert "intra-ocular".

UNITED STATES PATENT AND TRADEMARK OFFICE
CERTIFICATE OF CORRECTION

PATENT NO. : 5,344,448
DATED : September 6, 1994
INVENTOR(S) : Richard T. Schneider, et. al.

It is certified that error appears in the above-indentified patent and that said Letters Patent is hereby corrected as shown below:

Claim 1, Column 8, line 62, delete "intraocular", insert "intra-ocular".

Signed and Sealed this

Ninth Day of May, 1995

*Attest:*

BRUCE LEHMAN

*Attesting Officer*   *Commissioner of Patents and Trademarks*